United States Patent [19]

Leysen et al.

[11] Patent Number: 5,688,814
[45] Date of Patent: Nov. 18, 1997

[54] 4-AMINO-N-(4-METHYL-4-PIPERIDINYL)-2-METHOXYBENZAMIDES

[75] Inventors: Josepha Eduarda Maria Francisca Leysen, Oud-Turnhout; Georges Henri Paul Van Daele, Turnhout, both of Belgium

[73] Assignee: Janssen Pharmaceutica, N.V., Beerse, Belgium

[21] Appl. No.: 549,243

[22] Filed: Oct. 27, 1995

Related U.S. Application Data

[62] Division of Ser. No. 367,111, filed as PCT/EP93/01993, Jul. 8, 1993 published as WO94/02462, Feb. 3, 1994, Pat. No. 5,498,618, which is a continuation of Ser. No. 914,306, Jul. 17, 1992, abandoned.

[51] Int. Cl.[6] .................... A61K 31/445; C07D 211/56
[52] U.S. Cl. .................................... 514/329; 546/224
[58] Field of Search ............................ 546/224; 514/329

[56] References Cited

PUBLICATIONS

Azuma, C. "Marker reagents for detection of cell–surface receptors" CA 112:194927g, 1990.

Gaudreau, P. "Fluorophore–linked growth hormone–releasing factor analog for marking receptors on pituitary cell surface and treatment of wounds, diorders or diseases": CA 125:2280, 1996.

*Primary Examiner*—Ceila Chang
*Attorney, Agent, or Firm*—Charles J. Metz

[57] ABSTRACT

Piperidinyl substituted benzamides of formula

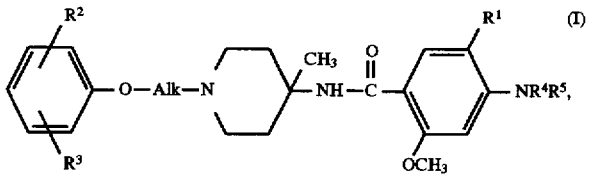

the pharmaceutically acceptable acid addition salts thereof and the stereoisomeric forms thereof, wherein $R^1$ is hydrogen or halo; $R^2$ is halo; $R^3$ is hydrogen or halo; $R^4$ and $R^5$ each independently are hydrogen, $C_{1-4}$alkyl or halo$C_{1-4}$alkyl; and the group $NR^4R^5$ may also be azido, Alk is $C_{2-4}$alkanediyl; pharmaceutical compositions containing said compounds of formula (I) as active ingredient; use of said compounds as a medicine; process of preparing said compounds; compounds of formula (I) containing a radioactive isotope; process of marking 5HT$_2$-receptor sites; and process for imaging an organ are disclosed.

4 Claims, No Drawings

4-AMINO-N-(4-METHYL-4-PIPERIDINYL)-2-METHOXYBENZAMIDES

CROSS-REFERENCE TO RELATED APPLICATIONS

This application is a division of application Ser. No. 08/367,111, filed on Jan. 6, 1995, now U.S. Pat. No. 5,498,618, which is a 371 of PCT/EP 93/01993, filed Jul. 8, 1993, published as WO94/02462, Feb. 3, 1994, which is a continuation of U.S. patent application Ser. No. 07/914,306, filed on Jul. 17, 1992 now abandoned.

BACKGROUND OF THE INVENTION

In U.S. Pat. No. 4,962,115 there are described N-(3-hydroxy-4-piperidinyl)benzamide derivatives having gastro-intestinal motility stimulating activity. In JP-A-2-104572 there are also described benzamide derivatives having digestive tract hypergic action. EP-A-0,278,173 discloses the use of heterocyclic derivatives of among others which are benzoic acid, acting as $5HT_3$-antagonists for treating depression.

The present compounds differ structurally and show unexpectedly high affinity as ligands for the $5HT_2$-receptor, yielding strong and specific $5HT_2$-antagonism.

DESCRIPTION OF THE INVENTION

The present invention is concerned with compounds having the formula

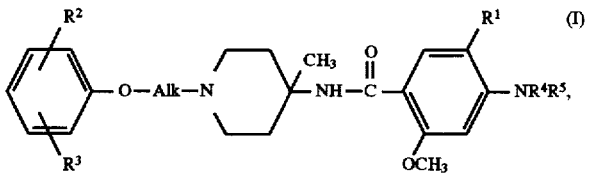

the pharmaceutically acceptable acid addition salts thereof and the stereoisomeric forms thereof, wherein $R^1$ represents hydrogen or halo;

$R^2$ represents halo;

$R^3$ represents hydrogen or halo;

$R^4$ and $R^5$ each independently represent hydrogen, $C_{1-4}$alkyl or halo$C_{1-4}$alkyl;

the group $NR^4R^5$ may also be azido; and

Alk represents $C_{2-4}$alkanediyl.

In the foregoing definitions and hereinafter halo defines fluoro, chloro, bromo and iodo; $C_{1-4}$alkyl defines straight and branch chained saturated hydrocarbon radicals having 1 to 4 carbon atoms such as, for example, methyl, ethyl, propyl, butyl, 1-methylethyl, 2-methylpropyl and the like; $C_{2-4}$alkanediyl defines bivalent straight or branch chained hydrocarbon radicals containing from 2 to 4 carbon atoms such as, for example, 1,2-ethanediyl, 1,3-propanediyl, 1,4-butanediyl and the branched isomers thereof.

The term "stereochemically isomeric forms" as used hereinbefore and hereinafter defines all the possible stereoisomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. The present invention clearly intends to embrace in its scope both the individual stereochemically isomeric forms as well as mixtures thereof.

It has to be understood that, when mixtures of enantiomers are present, they may be separated according to classical resolution methods, e.g. by fractional crystallization of their acid addition salts with a suitable chiral acid or by the separation by chromatography using a chiral phase.

The pharmaceutically acceptable acid addition salts as mentioned hereinabove comprise the therapeutically active non-toxic acid addition salt forms which the compounds of formula (I) are able to form. Said salts can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term add addition salt also comprises the hydrates and solvent addition forms which the compounds of formula (I) are able to form. Examples of such forms are e.g. hydrates, alcoholates and the like.

Interesting compounds are those compounds of formula (I) wherein $R^4$ and $R^5$ are hydrogen or wherein the group $NR^4R^5$ represents azido.

Particular compounds within the invention are those compounds wherein $R^2$ and $R^3$ are positioned in the 2- and 4-position of the phenoxy moiety; such compounds having more in particular a $R^2$ which is 4-fluoro; and/or wherein Alk is 1,3-propanediyl.

Particularly interesting compounds are those wherein $R^1$ represents a halo.

Preferred compounds are:
4-amino-N-[1-[3-(4-fluorophenoxy)propyl]-4-methyl-4-piperidinyl]-5-iodo-2-methoxybenzamide;
4-amino-5-chloro-N-[1-[3-(4-fluorophenoxy)propyl]-4-methyl-4-piperidinyl]-2-methoxybenzamide;
4-amino-5-bromo-N-[1-[3-(4-fluorophenoxy)propyl]-4-methyl-4-piperidinyl]-2-methoxybenzamide;
4-amino-N-[1-[3-(2-bromo-4-fluorophenoxy)propyl]-4-methyl-4-piperidinyl]-5-chloro-2-methoxybenzamide;
4-amino-N-[1-[3-(4-fluorophenoxy)propyl]4-methyl-4-piperidinyl]-2-methoxybenzamide;
4-azido-5-chloro-N-[1-[3-(4-fluorophenoxy)propyl]-4-methyl-4-piperidinyl]-2-methoxybenzamide;
4-azido-N-[1-[3-(4-fluorophenoxy)propyl]-methyl-4-piperidinyl]-5-iodo-2-methoxybenzamide;
4-azido-5-bromo-N-[1-[3-(4-4-fluorophenoxy)propyl]-4-methyl-4-piperidinyl]-2-methoxybenzamide, and the pharmaceutically acceptable acid addition salts thereof.

According to a further feature of this invention processes for the preparation of compounds of formula (I) are provided. The compounds of formula (I) may generally be prepared following art-known N-acylation procedures. For example, an intermediate of formula (II) is acylated with a carboxylic acid of formula (III), or a suitable reactive functional derivative thereof such as an acyl halide, symmetric or mixed anhydride and the like derivatives. Said reactive functional derivatives may be prepared following art-known methods and may be generated in situ, or if desired, be isolated and further purified before reacting these with intermediate (II). Alternatively, the intermediates (II) and (III) may be coupled in the presence of a suitable reagent, capable of forming amides, e.g. dicyclohexylcarbodiimide, 2-chloro-1-methylpyridinium iodide, 1,1'-carbonylbis[1H-imidazole], and the like reagents.

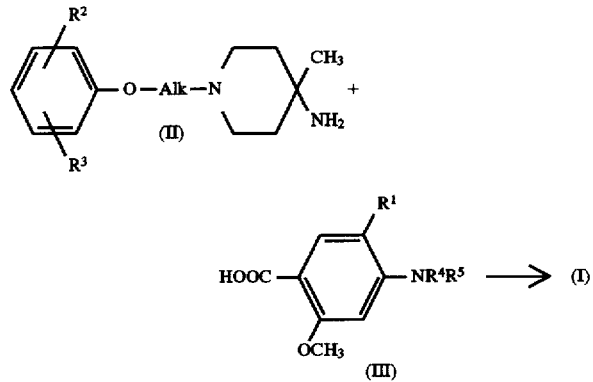

In the above and each of the following reaction schemes $R^1$, $R^2$, $R^3$, $R^4$, $R^5$ and Alk are defined as hereinabove under formula (I) unless otherwise mentioned.

Said N-acylation reaction may conveniently be carried out by stirring the reactants, preferably in a suitable reaction-inert solvent such as, for example, a halogenated hydrocarbon, e.g. dichloromethane; an aromatic hydrocarbon, e.g. methylbenzene; an ether, e.g. tetrahydrofuran; and the like. The water or acid that is liberated during the course of the reaction may be removed from the reaction mixture by art-known procedures such as, for example, azeotropical distillation, salt formation and the like methods. In order to pick up the acid which may be set free during the reaction a suitable base such as, for example, N,N-diethylethanamine, pyridine or N,N-dimethyl-4-aminopyridine may be added. Further, in order to enhance the rate of the reaction, said acylation reaction may advantageously be conducted at an elevated temperature, in particular the reflux temperature of the reaction mixture.

The compounds of formula (I) may also be prepared by N-alkylating an intermediate of formula (V) with a reagent of formula (IV).

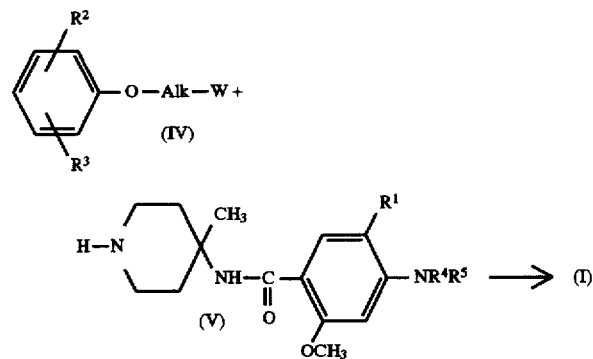

In formula (IV) W represents an appropriate reactive leaving group such as, for example, a halo, e.g. chloro, or a sulfonate, e.g. 4-methylbenzenesulfonate. Said N-alkylation can preferably carried out by stirring the reactants in a reaction-inert solvent such as, for example, an aromatic hydrocarbon, e.g. methylbenzene; an alcohol, e.g. 1-butanol; a ketone, e.g. 4-methyl-2-pentanone; an ether, e.g. tetrahydrofuran; a dipolar aprotic solvent, e.g. N,N-dimethylformamide, N,N-dimethylacetamide, dimethylsulfoxide; or a mixture of such solvents; at a temperature ranging from room temperature up to the boiling point of the reaction mixture. An appropriate base such as, for example, sodium or potassium carbonate, sodium hydrogen carbonate, N,N-diethylethanamine, may optionally be added to pick up the acid which is formed during the course of the reaction.

Still another procedure to prepare compounds of formula (I) is using an art-known O-alkylation procedure of a phenol of formula (VI), with an alkylating reagent of formula (VII). Said O-alkylation reaction is preferably carried out in reaction conditions which are similar to those used in the reaction of (IV) with (V).

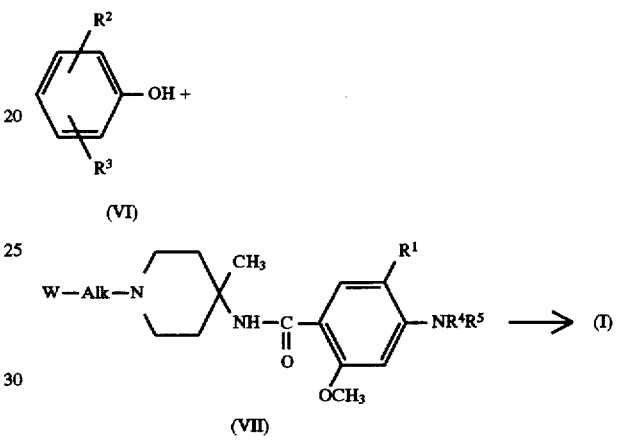

The compounds of formula (I) may also be prepared by methylating the corresponding 2-hydroxybenzamide analogues.

The compounds of formula (I) may also be converted into each other following art-known functional group transformation procedures.

a) The compounds of formula (I), wherein $R^4$ and $R^5$ are hydrogen can be transformed into compounds, wherein $NR^4R^5$ represents azido by reacting the compounds wherein $R^4$ and $R^5$ are hydrogen, with nitrous acid, thus forming an intermediate diazonium derivative, which is subsequently reacted with an azide, e.g. sodium azide. Said reaction can be performed by stirring the reactants in an appropriate reaction-inert solvent such as, for example, water, an alcohol e.g. methanol or ethanol; an ether, e.g. tetrahydrofuran; optionally in the presence of an acid such as, for example hydrochloric, hydrobromic, acetic or propanoic acid.

b) The compounds of formula (I), wherein $R^4$ and/or $R^5$ are hydrogen can be transformed into compounds, wherein $R^4$ and/or $R^5$ are $C_{1-4}$alkyl by art-known N-alkylation methods.

c) The compounds of formula (I) wherein $R^1$ is chloro, bromo or iodo; may be converted into compounds wherein $R^1$ is hydrogen following art-known hydrogenolysis procedures, i.e. by stirring and, if desired, heating the starting compounds in a suitable reaction-inert solvent in the presence of hydrogen and an appropriate catalyst such as, for example, palladium-on-charcoal and the like catalysts. The addition of a suitable base, such as, for example calcium oxide, potassium acetate or N,N-diethylethanamine and the like may be appropriate.

d) The compounds of formula (I), wherein $R^1$ is hydrogen, can be converted into compounds wherein $R^1$ is halo, using art-known halogenation procedures. Said halogenation can be performed by stirring the compounds of formula (I), wherein $R^1$ is hydrogen, with a halogen, e.g. bromine or chlorine, in an appropriate solvent such as for example water, an organic acid, e.g. acetic acid and the like. Optionally a catalyst can be used which may be iron, ferric chloride, ferric bromide and the like. Often a base can be applied to pick up the acid that is formed during the course of the reaction. Said halogenation procedure can also be performed with N-halo-amides, e.g. N-chloro-succinimide or N-bromo-succinimide, in a reaction-inert solvent such as, for example, acetonitrile or an ether, e.g. 1,4-dioxane, tetrahydrofuran and the like.

e) The compounds of formula (I) wherein $R^1$ is halo can be converted into each other using art-known halogen exchange reactions.

The intermediates used in the above reactions can be prepared by methods described hereinafter or art-known methods. For instance, the intermediates of formula (II) may be prepared by reacting an appropriately protected piperidine derivative of formula (VIII) with an intermediate of formula (IV) according to the procedure described herein above for the reaction of intermediate (IV) with (V); and subsequent deprotection. The protective group P may for example be a $C_{1-4}$alkylcarbonylgroup, which can be hydrolyzed according to art-known hydrolysis procedures.

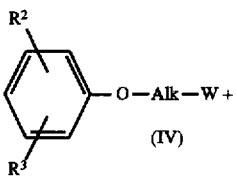

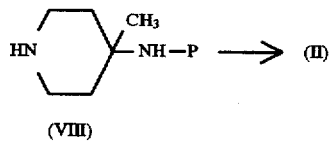

The intermediates of formula (III), wherein $R^1$ is halo, can be prepared by halogenating a amino-2-methoxy benzoic acid derivative, using the same halogenation methods as described hereinabove.

The compounds of the present invention are highly specific 5HT$_2$-receptor antagonists as is demonstrated in the pharmacological example 7. Due to said pharmacological activity the compounds of the present invention are useful in the treatment of a variety of conditions which are related to the excessive release of serotonin. Furthermore, the compounds of the present invention have a stronger peripheral than central pharmacological activity. Hence, they are useful in blocking serotonin-induced contractions of bronchial tissues and of blood vessels, arteries as well as veins (as is demonstrated in pharmacological example 8). Furthermore, 5HT$_2$-antagonists reportedly are effective in combatting psychoses, aggressive behaviour, anxiety, depression and migraine.

In view of their useful pharmacological properties, the subject compounds may be formulated into various pharmaceutical forms for administration purposes. Said pharmacological forms or compositions are deemed novel and consequently constitute another aspect of the present invention. Also the preparation of said compositions constitutes a further aspect of the present invention. To prepare the pharmaceutical compositions of this invention, an effective amount of the particular compound, in acid addition salt or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

The compounds of the present invention therefore may be used as medicines against above-mentioned conditions. Said use as a medicine or method of treatment comprises the administration of a compound of formula (I), a pharmaceutically acceptable salt or a stereoisomer thereof in an amount, effective to overcome said serotonin mediated conditions. In general it is contemplated that an effective amount would range from 0.1 to 100 mg/kg body weight and particularly from 1 to 20 mg/kg body weight. It is evident that said effective amount may be lowered or increased depending on the response of the treated subject and/or depending on the evaluation of the physician prescribing the compounds of the instant invention.

Due to their high degree of specificity to the 5HT$_2$-receptor, the compounds of formula (I) as defined above, are also useful to mark or identify receptors, in particular 5HT$_2$-receptors. To this purpose, the compounds of the present invention need to be labelled, in particular by replacing, partially or completely, one or more atoms in the molecule by their radioactive isotopes. Examples of interesting labelled compounds are those compounds wherein $R^1$ is a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using the procedures as described hereinabove to prepare halogen derivatives of formula (I). Preferred labelled compounds are those compounds of formula (I), wherein $R^1$ is a radioactive halo atom, especially $^{123}$I, $^{125}$I, $^{75}$Br, $^{76}$Br, $^{77}$Br or $^{18}$F.

Another interesting form of radiolabelling is the substitution of a hydrogen atom by a tritium atom or by substituting a carbon atom by a $^{11}$C-atom. Introducing such a $^{11}$C-atom is conveniently carried out by N-alkylating a compound of formula (I), wherein $R^4$ and/or $R^5$ are hydrogen using a $^{11}$C-labelled alkylating reagent, or by O-alkylating the 2-hydroxybenzamide analogues using a $^{11}$C-labelled alkylating reagent.

Hence, said radiolabelled compounds of formula (I) can be used in a process of specifically marking 5HT$_2$-receptor sites in biological material. Said process comprises the steps of (a) radiolabelling a compound of formula (I), (b) administering this radiolabelled compound to biological material and subsequently (c) detecting the emissions from the radiolabelled compound. The term biological material is meant to comprise every kind of material which has a biological origin.

More in particular this term refers to tissue samples, plasma or body fluids but also to animals, specially warm-blooded animals, or parts of animals such as organs. The radiolabelled compounds of formula (I) are also useful as agents for screening whether a test compound has the ability to occupy or bind to a $5HT_2$-receptor site. The degree to which a test compound will displace a compound of formula (I) from the $5HT_2$-receptor site will show the test compound ability as either an agonist, an antagonist or a mixed agonist/antagonist of a $5HT_2$-receptor. When used in in vivo assays, the radiolabelled compounds are administered in an appropriate composition to an animal, especially a warm-blooded animal, and the location of said radiolabelled compounds is detected using imaging techniques, such as, for instance, Single Photon Emission Computered Tomography (SPECT) or Positron Emission Tomography (PET) and the like. In this manner the distribution of $5HT_2$-receptor sites throughout the body can be detected and organs containing $5HT_2$-receptor sites such as, for example, the brain, can be visualized by the imaging techniques mentioned hereinabove. This process of imaging an organ by administering a radiolabelled compound of formula (I), which bind to the $5HT_2$-receptor sites and detecting the emissions from the radioactive compound also constitutes an aspect of the present invention.

The (radioactive) compounds of formula (I), especially the compounds containing an azidogroup can also be used in photoaffinity labelling and affinity chromatography.

In photoaffinity labelling, the marker, containing a photosensitive azido group, is bound covalently by irradiating the receptor/marker complex with UV-light. This irradiation induces the photolytical decomposition of the azidogroup, thus creating highly reactive radicals, which bind the marker covalently to the receptor. This irreversible covalent bond between the receptor and its radioactive marker allows characterization and detection of the receptor. What is more, this technique allows for the identification of the actual ligand binding site on the receptor. In affinity chromatography the marker is first bound, preferably in a covalent way, to a solid support, which then is used as a stationary phase for chromatographic purification of the receptor to which the marker specifically binds. Said chromatographic purification can be performed by passing a solution, containing the receptor, through a column of the marked stationary phase. The receptor is selectively removed from the solution by retention on the stationary phase and can subsequently be eluted by passing another solution, containing the marker, through the column.

The application of the compounds of formula (I) in the above described techniques constitutes a further aspect of the present invention.

The following examples are intended to illustrate and not to limit the scope of the present invention.

Experimental Part

A. Preparation of the Intermediates

EXAMPLE 1 a) A mixture of 18.5 g of N-[1-[3-(4-fluorophenoxy)propyl]-4-methyl-4-piperidinyl]acetamide and 310 ml of concentrated hydrochloric acid was stirred and refluxed for 24 hours. The reaction mixture was cooled and concentrated to a volume of about 100 ml. While cooling, the concentrate was treated with sodium hydroxide to pH 14. The product was extracted with dichloromethane. The extract was dried, filtered and evaporated. The residue was purified by column chromatography ($CHCl_3:CH_3OH(NH_3)$ 96:4 by volume). The pure fractions were collected and the eluent was evaporated. The residue was converted into the hydrochloride salt in 2-propanol. The salt was filtered off and recrystallized from 2-propanol, yielding, after drying in vacuo at 60° C., 6.4 g (29%) of 1-[3-(4-fluorophenoxy)propyl]-4-methyl-4-piperidinamine dihydrochloride monohydrate; mp 161.0° C. (interm. 1).

b) A mixture of 35.84 g of 1-(3-chloropropoxy)-4-fluorobenzene, 33 g of N-(4-methyl-4-piperidinyl)acetamide monohydrochloride, 54 ml of N,N-diethylethanamine, 0.1 g of potassium iodide and 1000 ml of N,N-dimethylformamide was stirred and heated for 1.5 hours at 70° C. The reaction mixture was cooled and the solvent was evaporated. The residue was taken up in a sodium carbonate solution in water and the product was extracted with dichloromethane. The extract was washed successively twice with water, twice with a sodium carbonate solution in water and again with water, dried, filtered and evaporated. The residue was purified by column chromatography ($CHCl_3:CH_3OH$ 95:5 by volume). The pure fractions were collected and the eluent was evaporated. The residue was crystallized from 2,2'-oxybispropane. The product was filtered off and dried in vacuo at 50° C., yielding 20.93 g of N-[1-[3-(4-fluorophenoxy)propyl]-4-methyl-4-piperidinyl]acetamide; mp. 103.4° C. (interm. 2).

c) A solution of 19 g of N-[1-(phenylmethyl)4-methyl-4-piperidinyl]acetamide hydrochloride in 400 ml of methanol was hydrogenated at normal pressure and at room temperature with 5 g of palladium-on-charcoal catalyst 10%. After the calculated amount of hydrogen was taken up, the catalyst was filtered off and the filtrate was evaporated, yielding 11.8 g of N-[4-methyl-4-piperidinyl]acetamide hydrochloride; mp. 230°–233° C. (interm. 3).

d) To a stirred and hot (60°–70° C.) mixture of 36 g of 4-methyl-1-(phenylmethyl)-4-piperidinol and 15 ml of acetonitrile were added dropwise 55 ml of concentrated sulfuric acid while cooling. After complete addition, stirring was continued for 20 hours at room temperature. The reaction mixture was poured on crushed ice. The whole was neutralized with potassium carbonate and then strongly alkalinized with a potassium hydroxide solution 15%. The free base was extracted with ethyl acetate. The aqueous phase was saturated with potassium hydroxide and extracted again with ethyl acetate. The combined extracts were dried, filtered and evaporated The semi-solid residue was triturated in 1,1'-oxybisethane and filtered. To the filtrate was added 2-propanone until a clear solution was obtained. Then gaseous hydrogen chloride was introduced into it. The precipitated solid salt was filtered off and recrystallized from 2-propanol, yielding 21.5 g of N-[1-(phenylmethyl)-4-methyl-4-piperidinyl]acetamide hydrochloride; mp. 288°–289° C. (interm. 4).

EXAMPLE 2

To a stirred and heated (25° C.) solution of 5 g of 4-amino-2-methoxy benzoic acid in 75 ml of 1,4-dioxane were added 6.9 g of grinded 1-iodo-2,5-pyrrolidinedione. The mixture was stirred in an oil bath at 105° C. for 3 hours. After the addition of 300 ml of water, the crystallized product was filtered off and dried, yielding 4.3 g (48.9%) of 4-amino-5-iodo-2-methoxybenzoic acid; mp. 180.6° C. (interm. 5).

B. Preparation of the Final Compounds

EXAMPLE 3

To a stirred solution of 3.5 g of intermediate (5) in 40 ml of dichloromethane were added dropwise 1.3 g of N,N-diethylethanamine at a temperature <5° C. After stirring for 10 minutes, 1.3 g of ethyl carbonochloridate were added dropwise. The reaction mixture was stirred for 1 hour at <5° C. and a solution of 2.7 g of intermediate (1) in 35 ml of dichloromethane was added at 10° C. After stirring overnight at room temperature, the mixture was washed with water, NaOH 5% and water, dried, filtered off and evaporated. The oily residue was crystallized from acetonitrile and water. The product was filtered off and dried, yielding 2.05 g (37.8%) of 4-amino-N-[1-[3-(4-fluorophenoxy)propyl]-4-methyl-4-piperidinyl]-5-iodo-2-methoxybenzamide; mp. 143.5° C. (comp. 1).

In a similar manner there were also prepared:

4-amino-5-chloro-N-[1-[3-(4-fluorophenoxy)propyl]-4-methyl-4-piperidinyl]-2-methoxybenzamide; mp. 118.0° C. (comp. 2);

4-amino-5-bromo-N-[1-[3-(4-fluorophenoxy)propyl]4-methyl-4-piperidinyl]-2-methoxybenzamide; mp. 139.7° C. (comp. 3); and 4-amino-N-[1-[3-(2-bromo-4-fluorophenoxy)propyl]-4-methyl-4-piperidinyl]-5-chloro-2-methoxybenzamide; mp. 156.9° C. (comp. 4).

EXAMPLE 4

A solution of 5 g of compound (3), 100 ml of methanol and 2 g of calciumoxide was hydrogenated With 2 g of palladium-on-charcoal catalyst 10%. After hydrogenation was completed, the catalyst was filtered off and the filtrate was evaporated. The residue was purified by HPLC [$H_2O$ ($NH_3$): $CH_3OH$: tetrahydrofuran (60:35:5)]. The desired fraction was collected and the eluent was evaporated. The residue was crystallized from a mixture of acetonitrile and water. The product was filtered off and dried, yielding 1.06 g (24.1%) of 4-amino-N-[1-[3-(4-fluorophenoxy)propyl]-4-methyl-4-piperidinyl]-2-methoxybenzamide; mp. 75.5° C. (comp. 5).

EXAMPLE 5

Compound (2) (0.006 mol) was dissolved in acetic acid 1N (600 ml) with stirring. The mixture was cooled on an ice bath till 5° C., sodium nitrite (2.07 g) in water (25 ml) was added and the mixture was stirred at 5° C. for 20 minutes. Sodium azide (1.95 g) in water (25 ml) was added dropwise at 5° C. (foam) and the mixture was stirred at 5° C. for 20 minutes NaOH 10N (66 ml) was added and filtered off. The precipitate was washed with water and air-dried, yielding 2.6 g (89%) of 4-azido-5-chloro-N-[1-[3-(4-fluorophenoxy)propyl]-4-methyl-4-piperidinyl]-2-methoxybenzamide hemihydrate; mp. 143.1° C. (comp. 6).

In a similar manner were also prepared:

4-azido-N-[1-[3-(4-fluorophenoxy)propyl]-4-methyl-4-piperidinyl]-5-iodo-2-methoxybenzamide hemihydrate; mp. 134.1° C. (comp. 7); and 4-azido-5-bromo-N-[1-[3-(4-fluorophenoxy)propyl]-4-methyl-4-piperidinyl]-2-methoxybenzamide (comp. 8); mp. 149.5° C.

C. Preparation of Radioactively Labelled Final Compounds

EXAMPLE 6

In a reaction vial 0.7 mg of compound (5) was dissolved in 0.5 ml of glacial acetic acid. 50 μl of radioiodide solution ($^{123}I^-$ in 0.1N sodium hydroxide) were added while stirring, followed by addition of 0.1 ml of 30% hydrogenperoxide. The reaction was allowed to proceed during 15–20 minutes at room temperature. The reaction vial was transferred to a small ice-bath. To the reaction mixture 2 ml of ice-cold water and 1.8 ml of 1M $Na_2SO_3$ were added while stirring and the pH was brought to 11 by addition of 2N sodium hydroxide. This solution was passed through a RP-Bondapack (100 mg) column using 10 ml of sodium hydroxide (pH 10.5) and 10 ml of distilled water. Compound (5) and the radioactive tracer were recovered in ±0.6 ml methanol. 0.3 ml of acetonitrile and 0.5 ml of water were added and the whole was filtered through a 0.45μ filter. The filtrate was purified by HPLC (eluent methanol/acetonitrile/water//trimethylamine//acetic acid 20/25/55//0.8/1.2; pH 4.8). The desired fraction was collected and ±20 ml of water was added. The solution was treated with a sodium hydroxide solution 2N to pH 11. This solution was passed again through a RP-Bondapack (100 mg) column using 10 ml of sodium hydroxide (pH 10.5)and 10 ml of distilled water. After blowing the column apparently dry, the radioactive tracer was recovered in ±0.5 ml of ethanol. Labelling yield: ±97%, overall radiochemical yield: ±75% of 4-amino-N-[1-[3-(4-fluorophenoxy)propyl]-4-methyl-4-piperidinyl]-5-iodo-2-methoxybenzamide, [5-$^{125}$I].

In a similar manner were prepared 4-amino-N-[1-[3-(4-fluorophenoxy)propyl]-4-methyl-4-piperidinyl]-5-iodo-2-methoxybenzamide, [5-$^{131}$I];

4-amino-N-[1-[3-(4-fluorophenoxy)propyl]-4-methyl-4-piperidinyl]-5-bromo-2-methoxybenzamide, [5-$^{76}$Br]; and 4-amino-N-[1-[3-(4-fluorophenoxy)propyl]-4-methyl-4-piperidinyl]-5-bromo-2-methoxybenzamide, [5-$^{77}$Br].

D. Pharmacological Example

EXAMPLE 7

Cell membrane fractions, prepared from tissue homogenates or cells, were incubated With a radioactive [$^3$H]-labelled substance (described hereinafter as the [$^3$H]-ligand) known to bind specifically to a particular receptor, thus labeling this receptor. The [$^3$H]-ligand used for each receptor site is mentioned in Table 1, as are the references wherein the experimental conditions of these tests are described.

After the incubation, the labelled membranes were harvested on glass fibre filters and rinsed twice with 5 ml of a cold buffer solution to remove non-bound [$^3$H]-ligands. Subsequently the glass fibre filters, with the harvested membranes, were placed in plastic mini-vials and 2.0 ml of Ultima Gold™ scintillation cocktail was added. Vials were vigorously shaken and kept at 4° C. for 24 h. Thereafter radioactivity was counted in a liquid scintillation spectrometer. Said radioactivity is proportional to the membrane labelling by the [$^3$H]-ligand. Specific membrane labelling by the [$^3$H]-ligand was distinguished from the non-specific membrane labelling by selectively inhibiting the labelling of the receptor site by another substance (unlabelled) known to compete with the [$^3$H]-ligand for binding to said receptor site. The remaining non-specific labelling was substracted from all assays concerning said receptor site.

To determine the receptor binding affinity of the non-radioactive compounds of the present invention, said compounds were added at various concentrations (ranging from $10^{-10}$ to $10^{-5}$M) to an incubation mixture containing the membranes and the [$^3$H]-ligand. During the incubation the test compounds were able to compete with the [$^3$H]-ligand for binding with the receptor. Subsequently the membranes were harvested and the radioactivity was measured as described above.

A compound having a high binding affinity is capable of displacing the [$^3$H]-ligand from binding to the receptor, and consequently the radioactivity of the harvested membranes will be diminished. Hence, by measuring the remaining radioactivity, one has a tool to measure the binding affinity of a test compound. The values presented in table 1 are IC$_{50}$-values, i.e. the molar concentrations at which the test compound was able to inhibit 50% of the [$^3$H]-ligand-binding In the table "5HT$_2$, 5HT$_{1A}$, 5HT$_{1B}$, 5HT$_{1D}$, 5HT$_{1C}$, 5HT$_3$" all refer to different types of serotonin receptor sites; "$\alpha_2$" refers to the $\alpha_2$-adrenergic receptor site; "H$_1$" refers to the histamine-H$_1$ receptor site; and "D$_2$" refers to the dopamine-D$_2$-receptor site.

TABLE 2

| Comp. No. | ED$_{50}$ (10$^{-10}$M) |
|---|---|
| 1 | 2.7 |
| 2 | 1.5 |
| 4 | 1.2 |
| 5 | 2.13 |

E. Composition Examples

EXAMPLE 9:

Film-Coated Tablets
Preparation of Tablet Core
A mixture of 100 grams of the A.I., 570 grams lactose and 200 grams starch was mixed well and thereafter humidified

TABLE 1

| Receptor site | labelled ligand | Compound number | | | | | | | ref |
|---|---|---|---|---|---|---|---|---|---|
| | | 1 IC$_{50}$ | 2 IC$_{50}$ | 3 IC$_{50}$ | 4 IC$_{50}$ | 5 IC$_{50}$ | 7 IC$_{50}$ | 8 IC$_{50}$ | |
| 5HT$_2$ | [3H]ketanserin | $10^{-9.22}$ | $10^{-9.60}$ | $10^{-9.18}$ | $10^{-9.20}$ | $10^{-9.75}$ | $10^{-8.13}$ | $10^{-8.45}$ | (a) |
| 5HT$_{1A}$ | [3H]8OHDPAT* | $10^{-6.34}$ | $10^{-6.18}$ | $10^{-6.39}$ | $10^{-6.38}$ | $10^{-5.65}$ | $10^{-7.05}$ | $10^{-6.66}$ | (b) |
| 5HT$_{1B}$ | [3H]serotonin | $10^{-5.05}$ | $10^{-5.18}$ | $10^{-5.18}$ | $10^{-5.00}$ | $10^{-5.00}$ | $10^{-5.49}$ | $10^{-5.48}$ | (c) |
| 5HT$_{1D}$ | [3H]serotonin | $10^{-5.53}$ | $10^{-5.26}$ | $10^{-5.56}$ | $10^{-5.46}$ | $10^{-5.16}$ | $10^{-6.37}$ | $10^{-6.02}$ | (d) |
| 5HT$_{1C}$ | [3H]mesulergine | $10^{-7.52}$ | $10^{-7.67}$ | $10^{-7.64}$ | $10^{-8.06}$ | $10^{-7.87}$ | $10^{-6.05}$ | $10^{-6.45}$ | (e) |
| 5HT$_3$ | [3H]GR65630** | $10^{-5.38}$ | $10^{-5.77}$ | $10^{-5.84}$ | $10^{-6.72}$ | >$10^{-5.00}$ | $10^{-5.00}$ | $10^{-5.08}$ | (f) |
| $\alpha_2$ | [3H]clonidine | $10^{-5.25}$ | $10^{-5.34}$ | $10^{-5.27}$ | $10^{-5.15}$ | $10^{-5.17}$ | $10^{-5.06}$ | $10^{-5.07}$ | (g) |
| H$_1$ | [3H]pyrilamine | $10^{-5.19}$ | $10^{-5.34}$ | $10^{-5.00}$ | $10^{-5.54}$ | $10^{-5.43}$ | $10^{-5.10}$ | $10^{-5.07}$ | (h) |
| D$_2$ | [3H]haloperidol | $10^{-7.56}$ | $10^{-7.53}$ | $10^{-7.32}$ | $10^{-7.64}$ | $10^{-7.07}$ | $10^{-7.18}$ | $10^{-7.20}$ | (i) |

(a) Leysen et al., Mol. Pharmacol. 21, 301–304, 1982;
(b) Fargin et al., J. Biol. Chem. 264, 14848–14852, 1989;
(c) Nelson & Taylor, Eur. J. Pharmacol. 124, 207–208, 1986;
(d) Waeber et al., Naunyn-Schmiedeberg's Arch. Pharmacol. 337, 595–601, 1988;
(e) Pazos et al., Eur. J. Pharmacol. 106, 539–546, 1985;
(f) Hoyer & Neijt, Eur. J. Pharmacol., 143, 191, 1987;
(g) Greenberg et al., Life Sci. 19, 69–76, 1976;
(h) Chang et al., Eur. J. Pharmacol., 48, 463–464, 1978; Laduron et al., Mol. Pharmacol. 21, 294–300, 1982;
(i) Leysen et al., Biochem. Pharmacol. 21, 307–316, 1978.
*8OHDPAT = 7-(dipropylamino)-5,6,7,8-tetrahydro-1-naphthalenol.
**GR 65630 = 3-(5-methyl-1H-imidazol-4-yl)-1-(1-methyl-1H-indol-3-yl)-1-propanone The specificity for serotonin 5HT$_2$ receptors of the compounds of the present invention is clearly demonstrated in the above table.

EXAMPLE 8

Antagonistic Activity on the Effect of Serotonin on the Caudal Artery of the Rat Caudal arteries from the fasted male rats (210–235 g) were used in the test. Two helical strips having a length of 5–6 cm and a width of 2 mm were obtained from each artery and mounted vertically in a 100 ml organ bath containing an oxygenated Krebs-Henseleit solution. Submaximal contractions of the arterial strips were produced by adding single doses of serotonin (40 ng/ml) to the organ bath for 2 minutes with each time an interval of 10 minutes. The amplitude of the contractions was measured before and 5 minutes after adding the drug. After washing out, the agonist was added again three times in order to see whether the contraction was restored and normalized. Table 1 shows the ED$_{50}$-values in M for a number of compounds of formula (I) in the above test. The ED$_{50}$-values are the minimal concentrations of the concerned drugs which reduce the amplitude of the contractions by at least 50% of its normal value.

with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane.

Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a mating apparatus.

EXAMPLE 10:

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A process of marking a 5HT$_2$-receptor with a radiolabeled compound comprising the steps of:

(a) radiolabeling a compound of the formula:

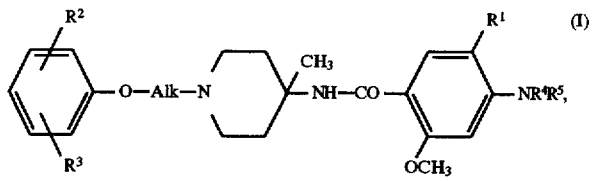

a pharmaceutically acceptable acid addition salt thereof or a stereoisomeric form thereof, wherein:

$R^1$ represents hydrogen or halo;
$R^2$ represents halo;
$R^3$ represents hydrogen or halo;
—$NR^4R^5$ represents azido; and
Alk represents $C_{2-4}$alkanediyl, (b) administering said radiolabeled compound to biological material,
   (c) irradiating the receptor/marker complex with UV-light, and
   (d) detecting the emissions from the covalently bonded radiolabeled compound.

2. A process according to claim 1 wherein the compound is 4-amino-N-[1-[3-(4-fluorophenoxy)propyl]-4-methyl-4-piperidinyl]-5-iodo-2-methoxybenzamide;

4-amino-5-chloro-N-[1-[3-(4-fluorophenoxy)propyl]-4-methyl-4-piperidinyl]-2-methoxybenzamide;

4-amino-5-bromo-N-[1-[3-(4-fluorophenoxy)propyl]-4-methyl-4-piperidinyl]-2-methoxybenzamide;

4-amino-N-[1-[3-(2-bromo-4-fluorophenoxy)propyl]-4-methyl-4-piperidinyl]-5-chloro-2-methoxybenzamide;

4-amino-N-[1-[3-(4-fluorophenoxy)propyl]-4-methyl-4-piperidinyl]-2-methoxybenzamide;

4-azido-5-chloro-N-[1-[3-(4-fluorophenoxy)propyl]-4-methyl-4-piperidinyl]-2-methoxybenzamide;

4-azido-N-[1-[3-(4-fluorophenoxy)propyl]-methyl-4-piperidinyl]-5-iodo-2-methoxybenzamide;

4-azido-5-bromo-N-[1-[3-(4-4-fluorophenoxy)propyl]-4-methyl-4-piperidinyl]-2-methoxybenzamide, or a pharmaceutically acceptable acid addition salt thereof.

3. A process according to claim 1 having at least one halo which is a radioactive isotope of iodine, bromine or fluorine.

4. A compound according to claim 1 wherein the compound is 4-amino-N-[1-[3-(4-fluorophenoxy)propyl]-4-methyl-4-piperidinyl]:5-iodo-2-methoxybenzamide, 5-$^{125}$I] or [5-$^{123}$I].

* * * * *